United States Patent
Eng et al.

(10) Patent No.: US 8,868,373 B2
(45) Date of Patent: Oct. 21, 2014

(54) ADJUSTABLE VIRTUAL REALITY SYSTEM

(75) Inventors: Kynan Eng, Zürich (CH); Pawel Pyk, Zürich (CH); Edith Chevrier, Zürich (CH); Lisa Holper, Zürich (CH); Daniel Kiper, Greifensee (CH)

(73) Assignee: Universitat Zurich Prorektorat MNW, Zurich (CH)

( * ) Notice: Subject to any disclaimer, the term of this patent is extended or adjusted under 35 U.S.C. 154(b) by 448 days.

(21) Appl. No.: 13/060,344

(22) PCT Filed: Aug. 19, 2009

(86) PCT No.: PCT/EP2009/006003
§ 371 (c)(1),
(2), (4) Date: Apr. 28, 2011

(87) PCT Pub. No.: WO2010/022882
PCT Pub. Date: Mar. 4, 2010

(65) Prior Publication Data
US 2011/0202306 A1    Aug. 18, 2011

Related U.S. Application Data

(60) Provisional application No. 61/091,470, filed on Aug. 25, 2008.

(51) Int. Cl.
*G06F 15/00*    (2006.01)
*A61F 4/00*    (2006.01)
*G06F 3/01*    (2006.01)
*A63F 13/20*    (2014.01)

(52) U.S. Cl.
CPC . *A63F 13/06* (2013.01); *A61F 4/00* (2013.01); *G06F 3/011* (2013.01); *G06F 3/017* (2013.01); *A63F 2300/1012* (2013.01)
USPC ............ 702/150; 128/899; 704/271; 252/500

(58) Field of Classification Search
CPC ........ A41D 19/0048; A41F 1/06; A01H 5/10; G09G 5/00; G09G 5/08; G06F 15/00; G06F 9/44; G06F 13/00; G06F 3/00; A63F 13/00; G01B 5/004; G01B 21/00; G06K 9/00
USPC ........... 702/151, 152, 150; 264/104; 252/500, 252/511; 704/270–271
See application file for complete search history.

(56) References Cited

U.S. PATENT DOCUMENTS 5,546,955 A    8/1996    Wilk
5,714,706 A    2/1998    Nakada et al.
(Continued)

FOREIGN PATENT DOCUMENTS

DE    102006040597    3/2008
JP    09-68973    3/1997
(Continued)

OTHER PUBLICATIONS

Input/Output Devices, machine Design, Penton Media, vol. 63, No. 13, Jun. 1, 1991. XP000349419.
(Continued)

*Primary Examiner* — Eliseo Ramos Feliciano
*Assistant Examiner* — Ruihua Zhang
(74) *Attorney, Agent, or Firm* — Cozen O'Connor

(57) ABSTRACT

Disclosed are virtual reality systems, in particular immersive virtual reality systems, their parts, construction and use. The systems and/or parts thereof may be used by adults or children, and may be adapted to support, often within a single device, a large range of users of different sizes and medical condition. Users with physical disabilities have difficulties using existing immersive technologies such as those using accessories like head-mounted displays and data gloves. Such users are provided with immersive virtual reality outputs that allow them to see virtual representations of their body parts which appear in a correct spatial position relative to the users' viewpoint.

34 Claims, 5 Drawing Sheets

(56) References Cited

U.S. PATENT DOCUMENTS

| | | | |
|---|---|---|---|
| 6,035,274 A * | 3/2000 | Kramer et al. | 704/270 |
| 6,148,280 A * | 11/2000 | Kramer | 702/153 |
| 6,515,669 B1 * | 2/2003 | Mohri | 345/474 |
| 7,667,891 B2 * | 2/2010 | Cok et al. | 359/443 |
| 2001/0034947 A1 | 11/2001 | Nagata | |
| 2003/0088294 A1 * | 5/2003 | Gesotti | 607/45 |
| 2005/0199250 A1 * | 9/2005 | Green et al. | 128/899 |
| 2005/0282633 A1 | 12/2005 | Nicolas | |
| 2006/0166737 A1 * | 7/2006 | Bentley | 463/30 |
| 2006/0176242 A1 | 8/2006 | Jaramaz et al. | |
| 2008/0136775 A1 * | 6/2008 | Conant | 345/156 |
| 2008/0143895 A1 * | 6/2008 | Peterka et al. | 349/15 |
| 2008/0258921 A1 * | 10/2008 | Woo et al. | 340/573.1 |

FOREIGN PATENT DOCUMENTS

| | | |
|---|---|---|
| JP | 2000-311047 | 11/2000 |
| JP | 2000-330567 | 11/2000 |
| JP | 2001-133300 | 5/2001 |
| JP | 2004-534316 | 11/2004 |
| JP | 2008-135033 | 6/2008 |
| WO | WO 03/005176 | 1/2003 |
| WO | WO 2006/086223 | 8/2006 |

OTHER PUBLICATIONS

International Search Report and Written Opinion dated Jun. 8, 2010.

* cited by examiner

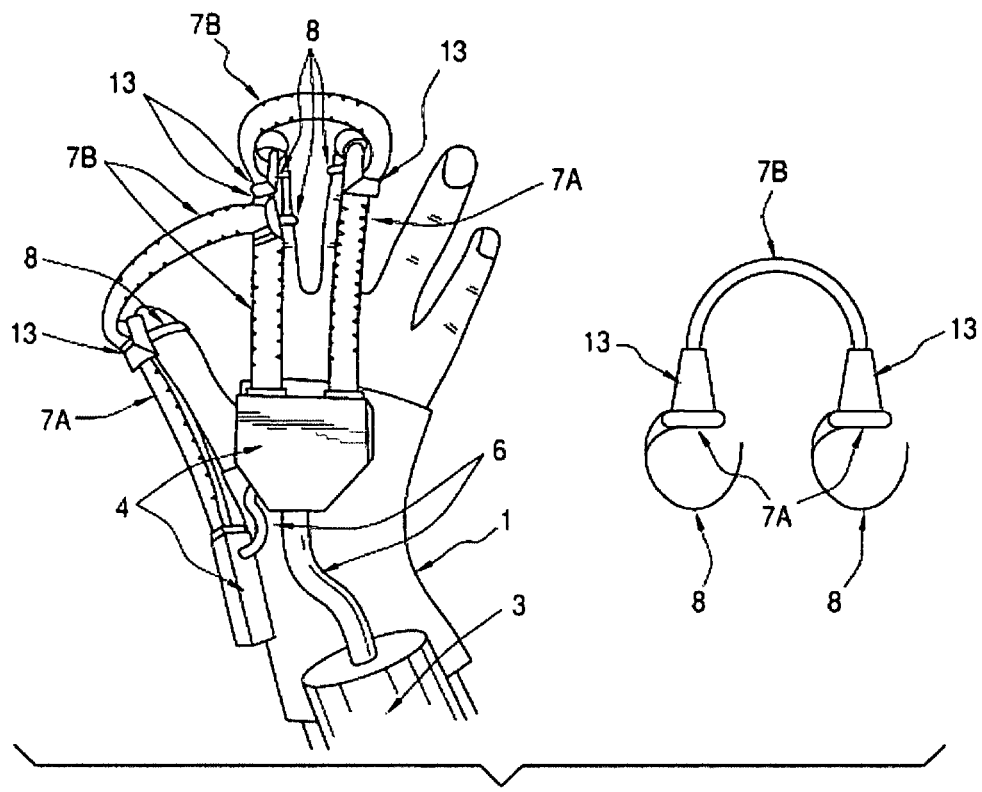
FIG. 3
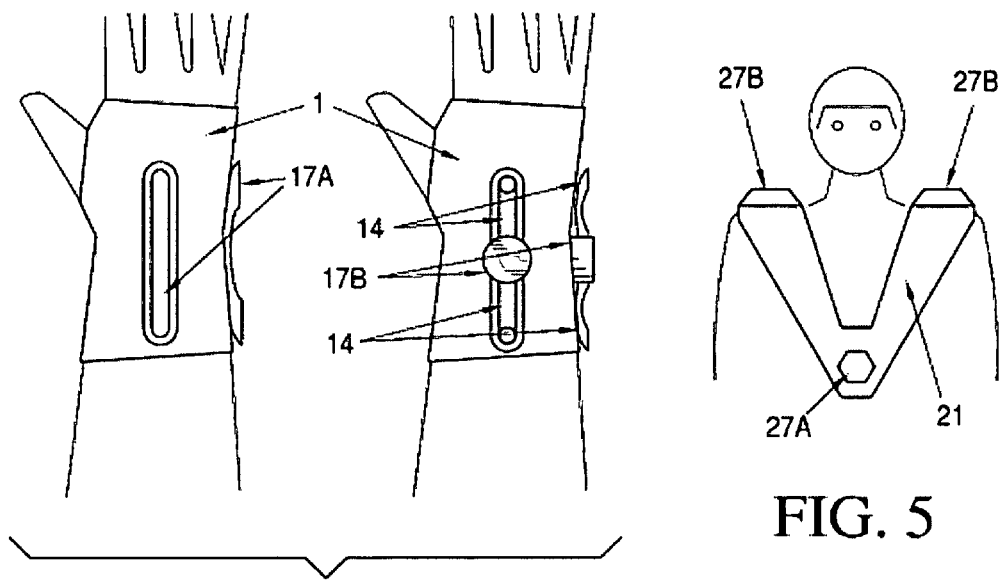
FIG. 4
FIG. 5

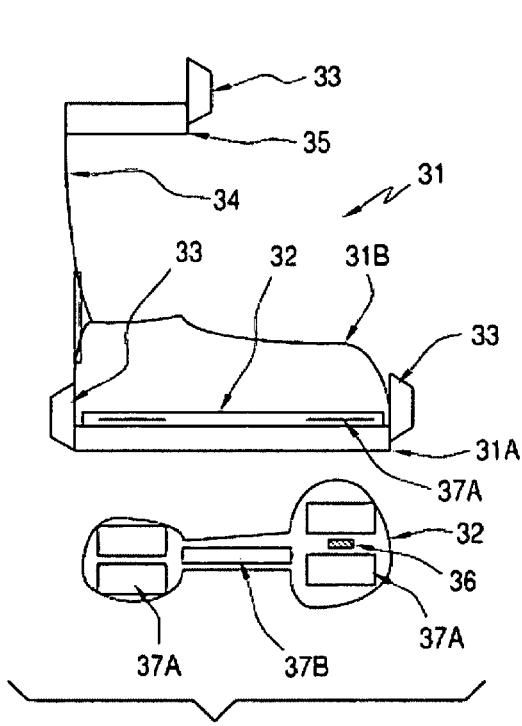
FIG. 6a
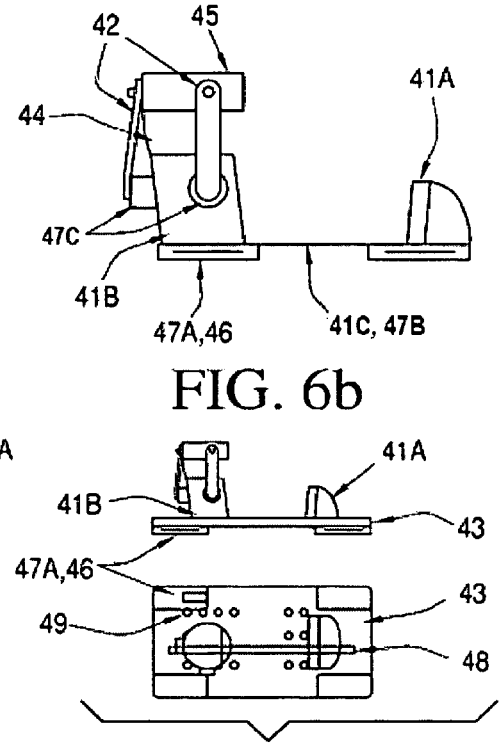
FIG. 6b
FIG. 6c
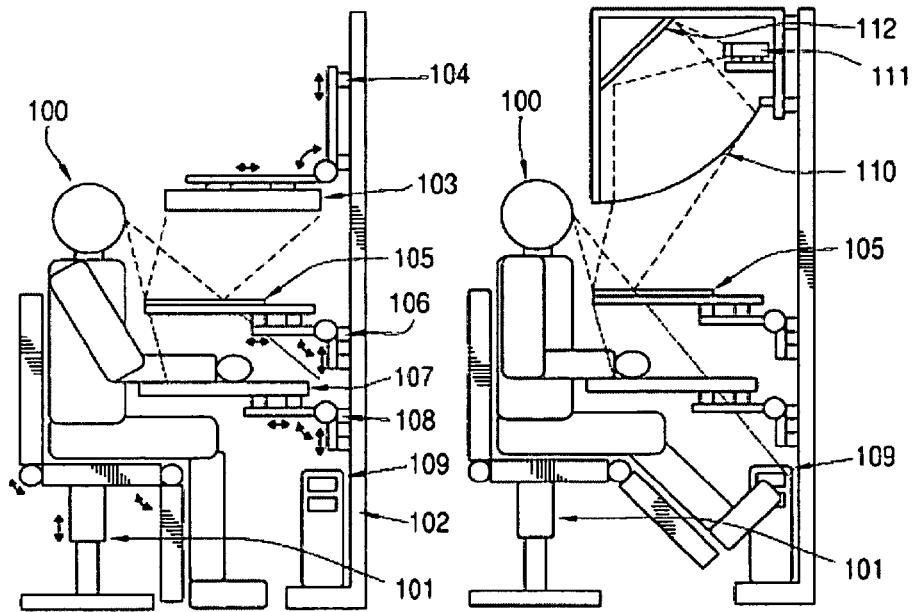
FIG. 7a
FIG. 7b

ADJUSTABLE VIRTUAL REALITY SYSTEM

PRIORITY CLAIM

This is a U.S. national stage of application No. PCT/EP2009/006003, filed on Aug. 19, 2009. Priority is claimed on the following application: U.S. Application No. 61/091,470 filed on Aug. 25, 2008, the content of which is incorporated here by reference.

FIELD OF THE INVENTION

This invention is directed towards virtual reality systems, in particular immersive virtual reality systems, their parts, construction and use. The systems and/or parts thereof may, in certain embodiments, be used by adults or children, and may be adapted to support, preferably in a single device, a large range of users of different sizes and medical condition. Users with physical disabilities have difficulties using existing immersive technologies such as those using accessories like head-mounted displays and data gloves. Such users are provided with immersive virtual reality outputs that allow them to see virtual representations of their body parts which appear in a correct spatial position relative to the users' viewpoint.

BACKGROUND OF THE INVENTION

A large number of virtual reality systems exist. Immersive virtual reality systems provide a sense of immersiveness (i.e., the sense or feeling of "being there"). They are used in entertainment, training of technical procedures or operation of machines, computer-aided design and rehabilitation of motor disorders or social disorders. However, generally these systems are designed for use by adult users with normal dexterity and range of limb movements. Problems arise, e.g., when existing virtual reality systems are used on children, or on adults who have severely limited limb movement (e.g. cramped hands), temporary or long-lasting physical deformities (e.g. swollen hands) or visual disorders (e.g. visual neglect, motion sickness).

Most virtual reality systems require the user to wear tracked devices such as data gloves to measure arm and hand movements. However, those data gloves with detailed finger bend tracking functionality cannot be easily adapted to fit the hands of either small children (e.g. approx. 5 years old upwards (e.g. glove size XS: 6-7, S: 8, M: 10-12, L: 14-16) or adults with deformities (e.g. swollen hands, cramped hands) without changing significant components of the system.

Certain prior art systems display some limited adaptability to the user that does not fit the norm.

U.S. Pat. No. 6,515,669 to Mohri, discloses a system having modular sensing components for the fingertips and the back of the hand. This system can be adapted to fit any sized hand by changing the underlying glove. However, the glove illustrated can only be fitted to healthy users with normal movement.

US Patent Publication No. 2008/0136775 to Conant discloses a system that uses finger—as well as wrist-mounted radio frequency identification (RFID) markers combined with a separate receiver that could also be used by users of any size. However, since there is no glove, large numbers of isolated tags need to be attached which are difficult to handle and require a long time to be fitted to a user.

The publications and other materials, including patents and patent publications, used herein to illustrate the invention and, in particular, to provide additional details respecting the practice are incorporated by reference.

Many available virtual reality systems use head-mounted displays (HMDs), either in form of opaque head-worn displays, translucent augmented reality displays or images projected on a translucent helmet worn by the user. Compared to normal flat displays, HMDs have the advantage of providing a fully immersive display (often in stereo 3D) with the virtual objects appearing to be in the correct spatial position relative to the user. Of particular importance is the ability to represent parts of the user's own body, usually the arms, torso and legs, in the correct spatial location. However, many users have difficulties using HMDs. To name just a few: subjects (healthy) or patients who are prone to motion sickness, claustrophobia or who have visual disorders such as visual neglect. While those users have the alternative to use conventional monitors or remote projection screens to circumvent their problem, these "solutions" come at the cost of not being provided with a spatially correct representation of their body parts.

In sum, current virtual reality systems are typically designed having healthy adults in mind. In addition, immersive virtual reality displays often use head-mounted displays, which are known to induce motion sickness-related nausea and are unsuitable for use by users with vision disorders or claustrophobia.

Thus, there is a need in the art to provide virtual reality environments useable by a wider range of subjects, including users with disabilities and/or those prone to motion sickness and/or claustrophobia as well as children.

The invention is, in certain embodiments, designed to overcome one or more of the shortcomings of the prior art.

BRIEF SUMMARY OF THE INVENTION

The invention provides, among others, (1) an immersive virtual reality system comprising one or more body sensor units and a display unit which allows viewing of virtual representations of parts of one's own body in the correct spatial locations relative to one's own viewpoint, and (2) a virtual reality system that can be quickly and easily adjusted for use by adults and children of different sizes. In certain embodiments, the invention provides a virtual reality system having one or more of the following advantageous features. In particular, the virtual reality system may be one that:
  does not cause motion sickness effects in users;
  allows free movements of the arms and legs while viewing virtual representations of the arms and legs;
  can be quickly and easily fitted to users with problems moving their hands, arms or legs;
  can be quickly and easily fitted to users with muscular disorders or deformities of the hands, arms or legs;
  contains a minimum number of discrete parts for ease of handling;
  can be easily constructed using existing display and sensing technologies.

The invention is, in one embodiment, directed at an adjustable body sensor unit comprising:
  at least one node comprising at least one sensor,
  at least one body attachment comprising at least one attachment element for attaching said at least one node to the body attachment,
  at least one element for communicating measurements received by the at least one sensor, wherein said element for communicating is preferably part of the node and wherein a location of the node on the body attachment is adjustable and/or the body attachment itself is adjustable to accommodate different users.

At least one further sensor/sensing element may be adjustably attached to the body attachment and the further sensor/sensing element may comprise a signal transducing element that measures a movement of a body part to which it is attached.

The body attachment may be an adjustable body attachment glove, which is preferably in the form of an open tube with a thumb-hole or in the form of a wrap around sheet. The at least one further sensor/sensing element may be a finger sensor or a wrist sensor. The glove may comprise one or more finger guides into which finger(s) of a user are inserted. The finger sensor or wrist sensor may be adjustably attached via the at least one attachment element, which may take the form of an attachment pad, clip, zip, buttonhole or pocket. At least one finger-to-finger sensor is also a part of the present invention, which is preferably securely attached to at least two finger sensor(s) and which connects a first finger to a second finger. The finger-to finger sensor may be part of the body sensor unit and may in this and other embodiments, be securely attached at each of its two ends to a finger sensor. The attachment glove is preferably elastic.

The transducing element may measure bending, rotation, elongation or pressure and may be a 2D or 3D accelerometer, a magnetometer, a potentiometer such as a bend, linear or rotary potentiometer, a position encoder or a pressure sensor. At least one effector such as a vibration motor, light and/or speaker, that preferably are part of the at least one node may also be part of the body sensor unit. The node may be self powered such as by an energy source such as a battery or a solar cell. The node may communicate with the base unit wirelessly such as via infrared or blue-tooth. The body sensor unit may have at least one finger base, which is preferably removably attached to the body attachment. The finger base may have at least one finger sensor attached to it, which runs along a finger. The finger sensor is preferably further secured to the finger(s) via sliding ring(s) at tip(s) of the finger(s). The sliding ring(s) may contain at least one marker to track positions of said tip(s). The finger sensor(s) may comprise an actuating device such as a linear motor or an electroactive polymer actuator. The body sensor unit may also comprise at least one marker for detecting
(a) a position, wherein the marker is preferably a magnetic field generator/detector, optical marker for an outside-in visual tracker, internal camera for inside-out visual tracker, ultrasonic emitter/receiver, radio transmitter/receiver,
(b) an orientation, wherein the marker is preferably a magnetometer or an accelerometer, and/or
(c) a temperature, wherein the marker is preferably a thermometer.

The body attachment may also be a vest. In this embodiment, the sensor may measure trunk movements and/or bending.

The body attachment may also be attached to a foot and measure foot movements, bending and/or forces. Here, the body attachment may comprise a heel and a toe element and at least one pressure sensor and/or bend sensor at a position for contacting an external surface. The body attachment may in particular be (a) an adjustable shoe or adjustable overshoe or sock, having a sole and an upper part, or (b) a toe and heel element which are adjustably attached to each other. Two pressure sensors may be located at the toe element and two pressure sensors may be located at the heel element. The pressure sensors may be integrated into an insert that is placed onto the sole inside the shoe and/or may be placed at or into an attachment outside the shoe such as at an inside of a heel or at or into a container at the toe region. The sensors may be removably attached to the sole.

The invention is also directed at an immersive virtual reality system that comprises at least one body sensor unit and a display unit as disclosed herein. The display unit may be in communication with the at least one body sensor unit to display movements of the body parts measured by sensors of the body sensor unit immersively.

The invention is also directed to a virtual reality system comprising
   at least one sensor or node comprising said at least one sensor, and
   at least one computer, wherein
   the sensor comprises a signal transducing element for attachment to a body part (e.g., hands, arms, legs and/or feet), wherein the transducing element is adapted to track movements of the body part,
   at least one element for communicating the tracked movements to the computer that maps the movements for display on a display unit, wherein the display unit comprises:
   at least one monitor,
   at least one mirror unit,
   an adjustment device to adjust the monitor and mirror unit to a position, in which the monitor is reflected in the mirror unit so that, in said position, movements tracked by the sensor are displayed on the monitor for immersive viewing in the mirror unit.

The mapping of the computer may include an amplification or reduction of the tracked movement. The monitor may display a mirrored image. The adjustment device may be a frame on which the at least one monitor, the at least one mirror unit and/or preferably at least one work surface are mounted. They may be adjustable in height and/or inclination. The monitor and/or the at least one mirror unit may be at least in part curved.

The invention is also directed at a body sensor unit comprising:
   at least one body attachment,
   at least one node comprising at least one sensor attached to said body attachment,
   at least one finger-to-finger sensor and an attachment element for connecting the finger-to-finger sensor between a first and a second finger, wherein the finger-to finger sensor comprises a signal transducing element that measures a movement of said first and second finger, and
   at least one element for communicating measurements received by said least one sensor and/or the finger-to-finger sensor.

The attachment elements may connect the at least one finger-to-finger sensor to at least two finger sensor(s) each extending along a finger.

The invention is also directed to the use of the body sensor unit and/or virtual reality system in the rehabilitation of patients with restricted movements in body part(s).

The invention is also directed to the use of the body sensor unit and/or virtual reality system by patients with motion sickness and/or visual disorders.

The invention is also directed to a method for creating an immersive virtual image of a body part comprising:
providing at least one tracking device, at least one monitor and at least one mirror unit,
wherein at least one sensor attached to the body part measures its movements,
wherein the monitor tracks the movements of the body part, and wherein the at least one mirror unit provides an immersive virtual picture of the body part.

In certain embodiments, at least two sensors are provided, one to measure arm and one to measure leg movements and the mirror unit and/or monitor may, at least in part, be curved and an immersive virtual image of the arm(s) and leg(s) may be created.

As the person skilled in the art will realize, the use of the virtual reality system described and claimed herein as well as its parts is vast and includes medical such as therapeutic (rehabilitation) uses as well as the non-medical uses mentioned above, which include, entertainment and training of technical procedures/the operation of machines as well as computer aided design. However, one preferred use of the virtual reality system disclosed herein is its use for rehabilitation of limb function in adults and children with various physical and neurological disorders. Typically, in rehabilitation the patient will see virtual representations of his/her arms and legs in the display, which are controlled by his/her real limbs via the body sensor units. The invention preferably transfers the tracked movements from the body sensor unit(s) to a virtual limb via a mapping function, which is varied according to the most appropriate course of therapy. In healthy subjects the mapping function is a simple one-to-one transfer of the real limb movements to the directly virtual limb movements, while in patients the mapping could be a possibly complex non-linear function including assisting (amplifying) or restraining particular movements according to both the type of injury and the stage of therapy. Also possible is the use of the movements of a real limb to (possibly partially) control a different virtual limb, which is of use when a patient has completely lost use of a limb or is completely missing a particular limb. It is notable that while the patient would normally be expected to control the movements of virtual limbs to carry out many different tasks (reaching and grasping, kicking, etc.), there is no requirement for virtual limbs to be displayed.

The embodiments listed herein can be seen as examplatory for certain objects of the invention. However, the person skilled in the art will understand that it is not necessary that any particular embodiment of the invention has any of the above-mentioned features neither is a possible embodiment of the invention limited to the listed features.

The foregoing features and advantages of the invention will be more readily understood upon consideration of the detailed description of the invention and the accompanying drawings.

BRIEF DESCRIPTION OF THE DRAWINGS

FIG. 3 depicts a body sensor unit for hands with extra measurement capabilities by an finger-to-finger sensor, an enlarged view of which is depicted on the left.

FIG. 4 shows a body sensor unit for wrists.

FIG. 5 shows a body sensor unit for a torso.

FIGS. 6A, B and C depict different body sensor units for the feet.

FIG. 7A shows an embodiment of a display unit.

FIG. 7B depicts an alternative display unit in which the embodiment of the monitor is such that the hands and feet of the user can be seen simultaneously at the correct perceived depth.

DETAILED DESCRIPTION OF VARIOUS AND PREFERRED EMBODIMENTS OF THE INVENTION

Figure 1:
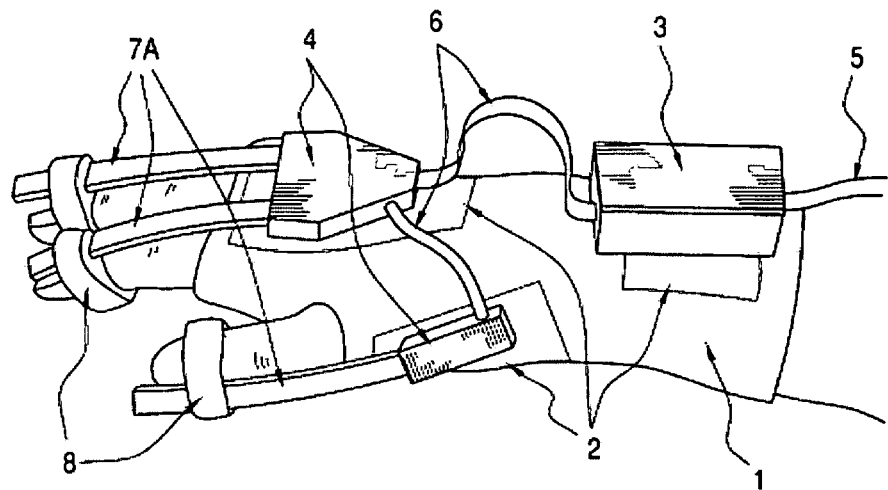
FIG. 1 depicts a body sensor unit for hands.

In one embodiment, the invention is directed at one or more body sensor units and/or a display unit. Specific embodiments of the body sensor unit are shown in FIGS. 1 to 5, while certain embodiments of the display unit are shown in FIGS. 6 to 10. Advantageously, the invention provides an immersive virtual reality system in which users of a wide variety of sizes and/or ages can see virtual representations of parts of their own body (e.g. arms and legs) in the correct spatial location relative to their real body parts, that is immersively. The immersive virtual reality system comprises at least a body sensor and a display unit. Both the body sensors and display unit are, in one preferred embodiment, designed to be easily adjustable for use by adults and/or small children, and for easy fitting to users with physical incapacities and impairments including, but not limited to, motor dysfunction or swollen or cramped limbs. However, in certain embodiments adjustability is not required.

In one embodiment, the body sensor units comprise a network of modular nodes, affixed to different parts of the body using highly adjustable body attachments. A network of modular nodes preferably contains 2, 3, 4, 5, 6, 7 or even more nodes. Each node contains one or more local sensors and/or effectors. Local sensors may include 2D or 3D accelerometers, magnetometers, potentiometers, position encoders and/or pressure sensors. However, as the person skilled in the art will readily understand, any device that is able to detect movement is a sensor suitable in the context of the present invention. Effectors, include, but are not limited to vibration motors, lights, speakers. However, as the person skilled in the art will readily understand, any device that is able to communicate directly with the user is an effector suitable in the context of the present invention. The nodes may, in certain embodiments, communicate with preferably one base unit, which in turn may communicate with a computer(s) controlling the rest of the virtual reality system. Elements for communicating may also be separate. Each node may be either connected to the base unit for communication and/or power supply, or it may be self-powered (using batteries, solar cells or any other energy source) and communicate, in certain embodiments, with the base unit, using, e.g., wireless technology, including, but not limited to, infra-red and Bluetooth.

The sensors/nodes are preferably attached to a body attachment designed to fit easily over a particular body part and which is adaptable to a wide range of sizes and/or shapes of the respective body part. In one embodiment, the body attachment is designed as a body attachment glove and has the form of an elastic tube, preferably of cylindrical form, with a side (lateral) hole for the thumb. In another embodiment, the body attachment takes the form of a wrap-around sheet with pockets for the fingers and thumbs. The wrap-around variant is especially advantageous as this wrap-around sheet ("glove") can generally be put on any patient regardless of hand cramps or deformities. To allow for relative movements of parts of the body sensor units at joints (e.g. bending in the fingers), parts of the body sensor unit may be designed to slide over the body (e.g. at attachment points for finger rings) while other parts may be fixed (e.g. at the back of the hand). In another embodiment, the body attachment has the form of a shoe or sock that the user wears barefoot or with socks. In still another embodiment the body attachment has the form of an overshoe that the user attaches to his or her own shoes. It is advantageous if the shoe or overshoe contains elastic or adjustable elements to allow easy fitting to a wide range of foot or shoe sizes.

In one embodiment, the sensing elements/sensors affixed to the body attachments are arranged to run along body parts and/or around the joint or body part whose angle(s) or expansion is to be measured. In another embodiment, they are arranged to measure relative displacements of body parts, e.g. between two fingers. In these cases the sensing elements/sensors may span the space between the two body parts, e.g. fingers. The sensing elements may also be in the form of active or passive markers for an external tracking device, e.g. camera-based.

The display unit may comprise a work surface, a mirror unit and a monitor that is preferably attached to a support frame. In this embodiment, the work surface, mirror unit and monitor may all be adjusted and rotated relative to the support frame. The work surface, mirror unit and monitor unit may be thin (10 mm to 2 cm, including 10 to 50 mm, 50 mm to 1 cm, or 1 cm to 2 cm) and flat, although in some embodiments of the invention the mirror unit or the monitor may be curved to confer, as described in more detail below, certain advantages in depth perception. In a typical usage scenario, the user sits in front of the display unit on an optional chair with his or her arms resting on the work surface, which is adjusted so that it is horizontal and at the same height as a normal table. The work surface is however, optional, and is preferably adjustable in height and inclination so that users in wheelchairs can be easily accommodated. The optional chair may have adjustable height, back inclination and lower leg support angle. However, the user may also stand or lie in front of the display unit.

The mirror unit is, in one embodiment, attached to the frame and is arranged horizontally, with the reflective surface facing upwards, preferably, approximately mid-way between the user's eye level and the work surface. However, in certain embodiments, the mirror unit may also be mounted elsewhere, such as on a carrier, which can be mounted on the users head and/or shoulders so that pictures of the monitor reflected in the mirror unit may be viewed by the user. The monitor is certain preferred embodiments set to be horizontal, facing downwards in front of and just above the user's head. By looking down into the mirror unit, the user sees the image of the monitor as if it was in the same plane as the work surface. By displaying on the monitor an image of virtual arms whose movements match the movements of the user's real arms as detected by the body sensor units, the user has the impression that the virtual arms are in the same physical location as his or her real arms and thus a sense of immersiveness. Several variations of this scenario are possible, including the user standing, lying down, or partially reclined so that he can see his feet. In each case the display unit is adjusted so that the virtual arms or legs appear in the "correct" location. If the monitor and/or the mirror unit are/is curved appropriately, it is possible to display both the arms and the legs in the correct virtual positions even though they are different distances away from the user's eyes. The monitor may also be combined with any three-dimensional display technology including, but not limited to, shutter glasses, tinted glasses or polarized filter glasses to give the viewer an impression of depth. The monitor of the display unit may also be composed of multiple flat or curved segments, and/or the mirror units may be composed of multiple flat or curved segments, so that parts of the virtual environment appear to be at a different depth relative to other parts of the virtual environment.

FIG. 1 illustrates an embodiment of the body sensor unit. The body sensor unit shown is used on a hand and is designed to be highly adjustable to fit different-sized hands as well as to readily fit hands which cannot easily wear regular gloves. A sleeve 1 is worn on the user's hands, which has on it one or more attachment pads 2. The sleeve 1 is made of a soft, breathable, lightweight, stretchable fabric such as neoprene, LYCRA, jersey, cotton or synthetic fleece to provide comfort during extended use. However, as the person skilled in the art will readily appreciate, the sleeve may be made of any other material and can contain any combination of multiple materials to optimize the comfort and support for the components of the body sensor unit. In one preferred embodiment, the sleeve is made from at least two materials of different flexibilities, or one material of variable flexibility, so that the sleeve is more flexible in the circumferential direction than in the longitudinal direction. In a preferred embodiment, the sleeve 1 is constructed as a shaped tube of fabric with a hole for the thumb, to allow maximum ease of fitting, in further embodiments it is shaped like a regular glove. However, the person skill in the art will appreciate that it can take many other forms. A node 3 and finger bases 4 are in FIG. 1 shown to be mounted on the attachment pads 2, which are preferably mounted above the back of the hand near the first knuckle, and near the base of the thumb. The attachment pads 2 are preferably made of VELCRO or any other adhesive material that allows the node 3 and/or finger bases 4 to be easily removed and repositioned to suit the hand shapes of different users. In addition, the node 3 may have attached to it one or more retaining straps to ensure that it is tightly attached to the forearm to prevent motion relative to the forearm during arm movement. A base cable 5 connects the node to the base unit (not shown), while one or more node cables 6 connect the node 3 to the finger bases 4. Finger sensors 7A are attached to the finger bases 4 at the bottom, and to finger rings 8 at the fingertips. The finger rings 8 fit around the user's fingers and are available in multiple sizes. They slide or are clamped over the finger sensors 7A. The finger sensors 7A may be made of a flexible material such as rubber or soft plastic, and/or may contain one or more articulated joints connected by flexures or any type of hinge to conform to the shape of a bending finger. If the outside of the finger sensors 7A is made of an easily deformable material then the hinges may not be necessary. The finger sensors 7A contain one or more signal transduction elements, typically bend sensors, or any other combination of devices for measuring the bending of the finger segments. The signal transduction elements may be placed inside the finger sensors 7A or may be even integrated into the finger sensors 7A, for example by embedding. In the embodiment shown three fingers are depicted; however, in general the invention can contain any number of finger sensors 7A (or none at all). Because the fixation of the finger bases 4 to the attachment pads 2 is fixed, it is preferred that the finger rings 8 can slide either relative to the finger sensors 7 or relative to the finger, to ensure that bending of the finger does not cause large stresses to build up in the finger sensors 7A which could lead to breaking of the finger sensors 7A or the connection to the finger bases 4. In embodiments in which the finger rings 8 slide relative to the finger sensors 7A, the contact areas between the finger rings 8 and the finger sensors 7A, are preferably selected to allow smooth sliding, e.g., the finger sensors 7A may be made of smooth plastic having a smooth plastic surface and finger rings 8 made of slightly loose fitting foam material or plastic.

The node 3 may contain one or more markers for detecting its own position (e.g., optical markers for an outside-in visual tracker, internal camera for inside-out visual tracker, ultrasonic emitter/receiver, radio transmitter/receiver), orientation (e.g. magnetometer and/or an accelerometer) or temperature (thermometer). The finger sensors 7A preferably contain transducers (transducing elements). There may also be marker(s) for detecting the posture of the fingers (e.g. one or more bend sensors, optical fiber sensor, markers for external outside-in visual tracking). One or more additional sensors may also be mounted longitudinally on the sleeve 1 at the wrist to measure wrist flexion and extension (not shown). In another embodiment, the finger rings 8 may contain active transducers (transducing elements) or markers (similar to the node 3) to track the positions of the finger endpoints. Many straightforward algorithms are known for determining the position and orientation of the arms and hands based on the readings of various tracking devices, for example double integration and gravity vector estimation for accelerometers, blob tracking for visual tracking devices, and time-of-flight for ultrasonic/optical/radio trackers (see, U.S. Pat. No. 6,256,046 for blob tracking, U.S. Pat. No. 5,510,800 for radio tracking, U.S. Pat. Nos. 4,980,871 and 5,495,427 for ultrasonic tracking; see, e.g., Schuon et al.; "High-quality scanning using time-of-flight depth superresolution", written at Anchorage, Ak., *IEEE Computer Society Conference on Computer Vision and Pattern Recognition Workshops,* 2008, Institute of Electrical and Electronics Engineers, pp. 1-7 (2008-07-15) for optical time-of-flight). In addition, well-known methods such as Kalman filters can be used for integrating the results of multiple (possibly conflicting) tracking data sources. The finger sensors 7A may also include any sort of actuating device (e.g. linear motor actuator, electroactive polymer actuator) for changing their shape and/or length for providing haptic feedback to the user's fingers. In addition, one or more of the finger rings 8, finger sensors 7A, finger bases 4 or the node 3 may optionally contain one or more devices such as vibration motors, lights and/or miniature speakers for providing feedback to the user. It is advantageous if all of the components and cable connections are sealed against dust and moisture for use in everyday environments and in harsh conditions, e.g. underwater.

Figure 2:
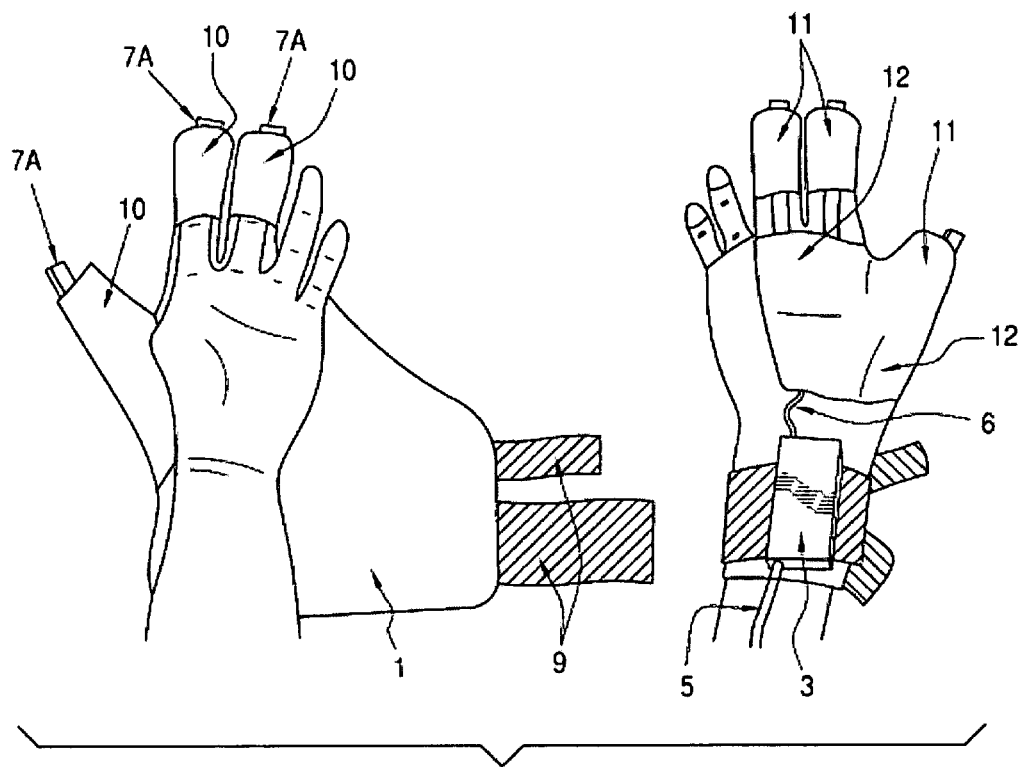
FIG. 2 shows a wrap around body sensor unit for hands.

FIG. 2 illustrates a further embodiment of the body sensor unit, in particular designed for easy fitting to hands onto which regular gloves do not easily fit. In this embodiment, the sleeve 1 is of an open wrap-around design, secured around the user's hand and wrist using one or more straps 9. The straps 9 are preferably made of VELCRO. However, the person skilled in the art will readily understand that the straps may be made out of other materials and that any arrangement that allows securing the sleeve around the hand may be employed, including button and button-hole combinations, press buttons, buckles etc. On the left hand of FIG. 2, an open hand view of the unassembled construct is shown, while the right hand side shows the assembled sleeve from a top perspective. The underside of the sleeve contacting the user's skin can optionally contain one or more integrated finger guides 10 into which one or more of the user's fingers or thumb are inserted. The finger guides 10 can be either open or closed at the tips. On preferably the opposite side of the finger guides 10 one or more finger sensor pockets 11 and/or finger base pockets 12 may be present, into which the finger sensors 7 and finger bases 4 (not shown, see FIG. 1) may be inserted. The finger base pockets 12 and finger sensor pockets 11 serve in the embodiment shown to hold the finger sensors 7A in position. The finger sensors 7A are preferably made of a smooth material such as plastic to allow sliding inside the finger sensor pockets 11 during finger bending, and are rigid enough to prevent buckling at the exposed region the finger sensor pockets 11 and the finger base pockets 12. The finger base pockets 12 are preferably open at the top to allow the finger bases 4 to be inserted, which are then preferably held in position between the finger sensors 7A via VELCRO or any other means. The node 3 may, e.g., be attached to the straps 9 using VELCRO or similar material, after the sleeve 1 has been wrapped around and secured to the user's hand and wrist. It is clear that, as an alternative to the finger sensor pockets 11 and finger base pockets 12, a combination of attachment pads 2 (compare FIG. 1) and finger rings 8 could also be used to keep the finger sensors 7A and finger bases 4 in the correct position relative to the user's hands.

Alternatively, and as will be described in more detail below, the sleeve 1 may also shaped similar to a sock with the heel and toes removed. The node 3 can, e.g., be affixed to attachment pads mounted on the leg or the top of the foot. Toe movement information can be recorded using modified smaller versions of the finger sensors 7A. In addition, modified versions of the finger sensors 7A attached to the top of the foot via the sleeve 1 can be used to measure bending of the foot and/or bending at the ankle.

FIG. 3 illustrates another embodiment of the invention, which optimally allows for measuring the motion of fingers relative to one another. In FIG. 3, the left side of the figure shows the full embodiment, while the right side shows a detailed view of only the components joining, in this case, the index and middle fingers. In this embodiment, finger-to-finger sensors 7B span the gaps between adjacent fingers. Shown are two finger-to-finger sensors 7B between the thumb and index finger, and the index finger and middle finger, respectively. While the finger sensors 7A shown in FIGS. 1 and 2 are arranged along the fingers extending preferably from the back of the hand/palm to the finger tips, the finger-to-finger sensors span from finger to finger preferably at the finger tips. An arrangement that includes the finger-to-finger sensors allows effective measurement of finger splay movements or thumb index finger abduction or adduction movements in the plane of the palm of the hand. In particular, the movement of the thumb can be more effectively measured in two degrees of freedom using an arrangement comprising the finger-to-finger sensors. The finger-to-finger sensors 7B are preferably securely attached to the existing finger sensors 7A running along the fingers such as via brackets 13. The brackets 13 ensure that the additional finger sensors 7B are kept substantially perpendicular to the longitudinal axis of the existing finger sensors 7A, that the finger-to-finger sensors 7B intersect the existing finger sensors 7A substantially perpendicular to the longitudinal axis of the existing finger sensors 7A. This arrangement has the advantage of keeping the finger-to-finger sensors 7B bent with a single radius of curvature, which is advantageous if the finger-to-finger sensor 7B comprises a resistive bend sensor which is only sensitive to bending in one direction. The arrangement shown, with brackets 13 on top of the finger sensors 7A running along the fingers, has the advantage of allowing the fingers to move freely together: Most grasping actions can be carried out without obstruction by the sensors. The brackets 13 can be either fixed to the finger rings 8, or mounted separately (either adjustably or permanently) to the finger sensors 7A. Adjustable fixation of the brackets allows for an optimal placement of the finger-to-finger sensors 7B for measuring relative finger movements. The brackets 13 can alternatively also be attached, either adjustably or permanently, to any of the finger bases 4. In one aesthetically pleasing design, the wires from the finger-to-finger sensors 7B may be routed through the finger sensors 7A running along the user's fingers. If appropriate, the finger-to-finger sensors 7B can also carry conductors for electrically connecting the finger bases 4, eliminating the need for separate node cables 6. While the embodiment shown only measures the movements of three fingers, it is clear that any combination of the fingers can be measured using the described components of this embodiment.

FIG. 4 shows an embodiment of the invention for measuring wrist movements which is advantageously integrated with elements from one or more of the other embodiments shown in FIGS. 1 to 3. Here a fabric sleeve 1 worn on the hand encloses the wrist; it may be, e.g., of the type shown in FIG. 1 or FIG. 2. Attached to the sleeve using VELCRO or any other attachment method (e.g. sewn-in pockets) are one or more sensors 17A that measure wrist movement, in particular bending and/or rotation of the wrist. These "wrist sensors" 17A are preferably mounted as shown to independently measure wrist flexion/extension and wrist rotation about orthogonal axes, although they may also be mounted in any other orientation. A wide array of sensor types and sensor arrangements are within the scope of the present invention. If resistive bend sensors 17A are used, it is usually advantageous to use two sensors mounted back-to-back within a single sensor unit, as resistive bend sensors are often only sensitive to bending in one direction. Alternatively, bend sensors 17A may also be mounted on opposing sides of the wrist to enable bending in both directions to be measured. Another method of transducing the rotation at the wrist is to use a rotation sensor 17B connected to struts 14. The struts 14 are, in turn, connected to the fabric sleeve 1. The rotation sensors 17B are preferably placed at the axes of rotation of the wrist. Thus, in one advantageous embodiment, the struts 14 are position-adjustable on the sleeve for each individual user. The struts 14 are preferably designed to allow bending out of the plane of rotation of the rotation sensors 17B to accommodate out-of-plane wrist bending, but are rigid in the plane of rotation of the rotation sensor 17B to effectively transmit the wrist movement to the rotation sensor 17B. As the person skilled in the art will appreciate, a wide array of technologies can be used to transduce the wrist movements, such as, but not limited to, resistive potentiometers or optical position encoders.

The person skilled in the art will appreciate that the above described measurement of wrist movements can be easily adapted and used at any other movable joint of the body, such as the elbow, knee, ankle, hip, neck or shoulder.

FIG. 5 shows an embodiment of the invention for measuring trunk movements. A vest 21 is worn on the torso. Attached to the vest 21 are one or more sensors/nodes 27A/B. It is advantageous if the vest 21 can be simply placed over the user's head so that no sleeves are required. It is also advantageous if the positions of the sensor/nodes are adjustable using any method, including but not limited to fasteners such as VELCRO, pockets, strip fasteners buttons, etc. In one of many typical arrangements, one sensor containing unit is placed on each shoulder of the vest and one is placed on the chest. However, embodiments using one, two, four, five, six or more sensor containing units are within the scope of the present invention. The sensor/nodes may be placed in different locations depending on the application.

FIG. 6 shows three embodiments for measuring foot movements and/or forces. FIG. 6A depicts a version designed for users who are either barefoot or wearing socks. The user puts on a shoe comprising a sole 31A and a upper part 31B of the shoe, which may be designed in any way to facilitate comfortable and easy wearing. Depending on the type of desired interaction, the sole 31A may be of a variety of shapes and textures, it may also be, e.g., on the outside smooth or have wheels, even ice skate blades or other attachment thereon. An insert 32 inside the shoe preferably contains several sensing and actuating units. The insert 32 may optionally be combined with the sole 31A. An optional flexible band 34 may connect the upper part 31B of the shoe 31 to a leg strap 35, which is wrapped around the user's leg at any comfortable height and secured using any suitable means (e.g. buckle, VELCRO). The insert 32 may have embedded in it one or more pressure sensors 37A. The pressure sensors 37A may be of any size, shape and distribution, although a typical arrangement as shown comprises two sensors near the toes and two near the heel so that shifts in body weight can be detected. In addition, one or more vibration feedback elements 36 may be embedded in the insert 32. The vibration feedback element 36 may be based on an electric motor, piezo actuator or any other device. One or more bend sensors 37B may also be mounted in or at the insert 32 to measure flexion of the foot, and also on the shoe upper 31B and the flexible band 34 to measure ankle flexion and extension. One or more sensor containing units 33 may also be mounted anywhere on the shoe. Each sensor containing units may comprise in addition to one or more transducing elements, markers and/or effectors, such as accelerometers, magnetometers, infra-red LEDs or ultrasonic emitters for external tracking, vibration feedback, audio speakers, optical markers, etc.

FIG. 6B depicts an overshoe designed for users to wear barefoot or with socks or to slip on over their own shoes. The user's shoe is held by a toe element 41A and a heel element 41B, which are connected by a shank 41C. The toe element 41A reaches over the front of the toe of the user's shoe to prevent it from slipping off. It can be advantageous if one or more of the toe element 41A, heel element 41B and shank 41C is made of a flexible material such as rubber, so that the overshoe can fit a range of shoe sizes and is held securely. Any sensor and/or node and/or effector and/or marker can be mounted on or embedded in the toe element 41A, heel element 41B and/or shank 41C, such as, to provide just one example, one or more pressure sensors 47A, vibration feedback elements 46 (markers) or bend sensors 47B. A flexible band 44 may be optionally attached to the heel element 41A, connected to a leg strap 45. One or more rotation sensors 47C may be optionally mounted on the heel element 41A and may be connected to the leg strap 45 via a strut 42. The connection between the strut 42 and the leg strap 45 may be either fixed or pivotal, and the point of connection may be adjustable. The position of the rotation sensors 47C is preferably adjustable to match the ankle rotation points of different users. The strut 42 may be designed to be rigid in the plane of rotation of the rotation sensor 47A, but to allow bending out of the plane to accommodate movement of the ankle. The rotation sensors 47C can use any suitable technology to measure the rotation, including but not limited to, transducing elements such as potentiometers and/or rotary optical position encoders. In both versions of the embodiment, the cables connecting the components can be discrete and/or embedded in the different structural parts of the shoe.

The embodiment shown in FIG. 6C somewhat resembles FIG. 6B, but provides for a different method for adjusting the body sensor unit to different foot sizes. The toe element 41A and heel element 41B are attached to a baseplate 43. The baseplate 43 is large enough to accommodate a wide range of foot sizes. It preferably also allows positioning of the toe element 41A and heel element 41B at multiple positions on the baseplate 43, facilitating different body movements by changing the relationship between the contact area of the foot with the baseplate 43 and the ground, thus changing position of the user's center of gravity relative to the baseplate 43. Any sensing and/or feedback elements can be incorporated into the baseplate 43; In the embodiment shown, pressure sensors 47A and vibration feedback elements (markers) 46 are attached to the corners of the baseplate 43. The toe element 41A and/or the heel element 41B may or may not be position-adjustable using a variety of ways. To describe just one embodiment, the toe element 41A and heel element 41B may be attached to a rail 48, which permits sliding of the elements for size adjustment, and which can be locked into place using a wide variety of ways. The rail may be either cut into the baseplate 43 or raised from the baseplate 43, or a combination of both. The toe element and heel element may also incorporate parts which allows them to be located and secured at any part of a hole array 49. The person skilled in the art will appreciate that other method/devices, e.g. straps or locking tabs, can be used to secure the toe element 41A and/or the heel element 41B to the baseplate 43 in a way that is either fixed or adjustable.

Although the embodiments of the body sensor units described above and in particular shown in FIGS. 1 to 6 illustrate specific uses of body sensor units on the specific body parts, it is clear that they can be readily adapted for use on other body parts such as different parts of the leg, arm, neck and head.

FIG. 7a illustrates an embodiment of the display unit. The user is seated on a chair 101, which is optionally height and/or angle adjustable, in front of the display unit. The display unit comprises a frame 102, upon which a wide variety of items may be mounted. Shown is a monitor 103 that is attached to a monitor mount 104, which allows the monitor 103 to be adjusted in its height, horizontal position and angle. A mirror 105 is attached to a mirror mount 106 in a similar way, preferably below or adjustable to be below, the monitor mount 104. While optional, a horizontal work surface 107 is, in the embodiment shown, attached to a work surface mount 108 below the mirror mount 106. The monitor mount 104, mirror mount 106 and work surface mount 108 are all shown to be attached to the frame 102. A control computer 109 may be attached to the frame 102 or placed elsewhere, and is used to control the image on the monitor 103 and to read the input data from the body sensor units. The mechanisms for the monitor mount 104, mirror mount 106 and work surface mount 108 can be fixed, manually or otherwise adjustable via any combination of actuators, levers, ropes, or any other mechanical or electrical device. As can be seen from the following Figures, in one preferred embodiments the relative position of, in particular, the monitor 103 and mirror 105 can be varied to accommodate a wide variety of uses.

If the mirror 105 is arranged approximately horizontally, facing upwards approximately mid-way between the user's eyes and the work surface 107 (or the location of the hands), and the monitor 103 is arranged just above the user's head, facing downwards, the user will, when he/she looks into the mirror 105, see a mirror image of what is displayed on the monitor 103, appearing to float in the same plane as the work surface 107 where his/her hands are resting. If the user wears body sensor units on each hand (FIG. 1), the movements of the user's real arms and hands can then be transferred to the (mirrored) image displayed on the monitor 103 as viewed in the mirror 105 as virtual arms and hands. If arms are displayed on the monitor 103, the user will, when looking into the mirror, have the sensation that the virtual arms are in the same physical location as his/her own real arms.

For example, for a typical user approximately 160-190 cm tall sitting with their eye level approximately about 120-130 cm above the ground and their arms on a work surface approximately 80 cm above the ground, a horizontal mirror placed facing upwards approximately 20-30 cm above the work surface will reflect the image from a horizontal downwards-facing monitor approximately 45-60 cm above the work surface to an approximately correct location. Another working and viewing position, which may be more comfortable for some users, can be obtained if the work surface, mirror unit and monitor are all tilted approximately 10-20 degrees towards the user. Yet another working and viewing position can be achieved by placing the mirror about 10 cm below the user's eye level, which corresponds to a monitor position of about 60-80 cm above the work surface; one advantage of this arrangement is that the user has more space for free arm movements and there is a higher clearance to the monitor above the user's head (see, e.g., FIG. 10C).

Several variants on the components in this embodiment are possible, which are all part of the invention. For example, the mirror 105 may be flat as shown in FIG. 7A, or curved in any way or may be part of a prism (FIG. 10C). The monitor 103 may be curved (see FIG. 7B) and/or designed to display three-dimensional images, possibly in conjunction with shutter glasses, tinted glasses or any other three-dimensional display technology. The mirror or prism may, in a preferred embodiment, be attached to a support worn on the user's head or shoulders (FIG. 10A to FIG. 10C). In such an embodiment the plane of the mirror or prism is in the lower half of the user's field of view. The function of the mirror is the same as in the other embodiments. The advantages of a head- or shoulder-worn mirror include the need for only a very small mirror (maximum size approximately 25 cm×8 cm), more free working space for the user's arms and an increased clearance above the user's head to the monitor. Generally, the shoulder-worn arrangement is preferable to the head-worn arrangement for users with motion sickness problems as movements of the head in the shoulder-worn arrangement will not lead to corresponding disorienting movements of the viewed scene.

In a preferred embodiment, the work surface 107 is made of a thin, hard, flat, rigid material or combination of materials similar to a normal table top. A total thickness less than 3 cm is preferred. In other embodiments, it may have any shape to accommodate particular applications, and may additionally contain any input/output devices mounted on it that are also optionally represented in the virtual environment. When using optical tracking devices on the user's arms or on other objects on the table, it is advantageous if the work surface 7 is made of a translucent or transparent material to allow reflected or emitted light to pass through.

FIG. 7b illustrates an alternative embodiment of the display unit, designed for simultaneous viewing of the virtual arms and legs at the correct perceived locations. The user's chair 101 is adjusted so that the legs extend forwards so that the user's feet would be visible to the user if the display unit was not present. The image is shown to the user on a curved screen 110 which is closer to the mirror 105 near the user (where the arms are shown) and further away from the mirror 105 away from the user (where the legs are shown). The curvature of the screen is preferably set so that the half of the screen closest to the user (where, e.g., the arms are displayed as flat as possible, so that the apparent depth of the image is approximately constant and matches that of the work surface. The curvature of the half of the screen further from the user is preferably set so that the knees appear slightly further away from the user than the hands, and the feet appear approximately twice as far away. This means that if the edge of the screen closest to the user is flat (0 degrees), then the edges of the screen furthest from the user in the embodiment shown will be approximately 25-40 degrees.

The image displayed on the curved screen 110 is geometrically adjusted, that is, the image displayed on the curved screen 110 is shown in a distorted form, with the distortion achieved using standard graphics driver software or any known optical method, so that an un-distorted representation appears to the user when viewed in the mirror 105. While the image on the curved screen 110 can be implemented using any current or future technology, typically it would be done by using translucent material for the curved screen 110 and back-projecting the image onto the curved screen 110 using a standard video projector 111 connected to the control computer 109. Optionally, a projector mirror 112 can be used to aid in the advantageous positioning of the video projector 111 by reflecting the outgoing beam of light onto the curved screen 110. Note that the curved screen 110 can also be flat, in which case this embodiment is equivalent to the embodiment in FIG. 7*a*. The curved screen 110 may also be combined with two video projectors 111 with perpendicular polarizing filters fitted in front of them so that a user wearing appropriately matched polarizing glasses can see a three-dimensional image on the screen.

A variation of the embodiment in FIG. 7*b* uses a curved mirror instead of a curved screen. This variation allows a standard flat-screen display to be used to achieve an equivalent effect. Another variation uses a screen or mirror which is curved about a horizontal axis aligned in the direction of the patient's view, instead of the curvature about the transverse axis (through the patient's ears) shown in FIG. 7*b*. This alternative allows, for example, the user's legs and feet to appear further away in the virtual image in the center of the image, while the arms on the left and right side of the image appear closer to the viewer.

Figure 8A:
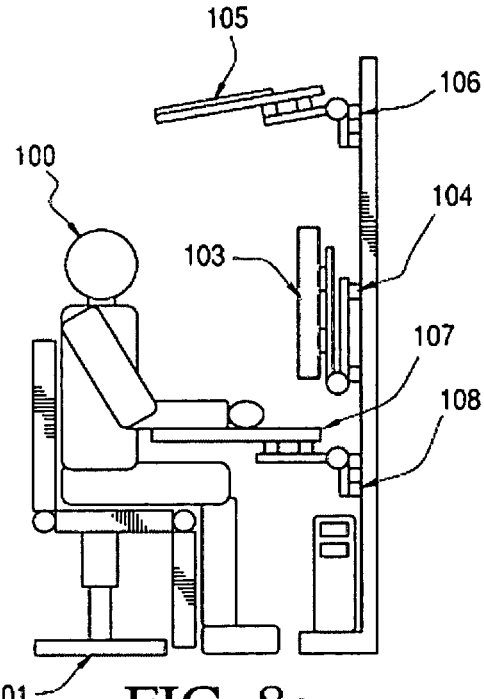
FIG. 8A shows a display unit adjusted for use in a seated viewing mode.
Figure 8B:
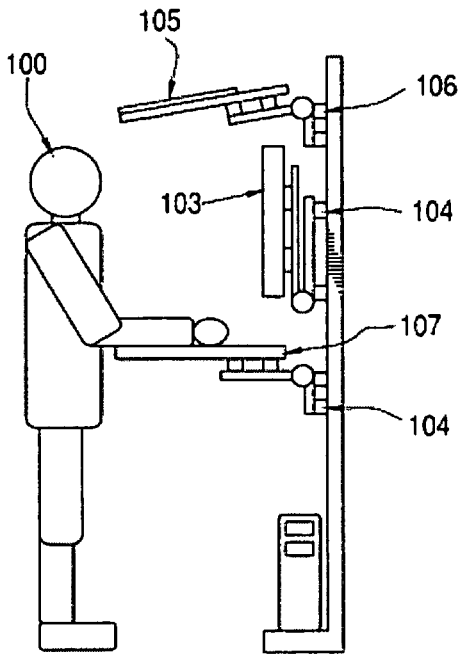
FIG. 8B shows a display unit adjusted for use in a standing viewing mode.

FIGS. 8*a* and 8*b* show alternative arrangements of the embodiment of the display unit shown in FIG. 7*a*, with the system components rearranged for conventional viewing of the monitor 103. In FIG. 8*a* the user 100 is using the display seated in the chair 101 in a normal desk arrangement, while in FIG. 8*b* the user is standing.

Figure 9A:
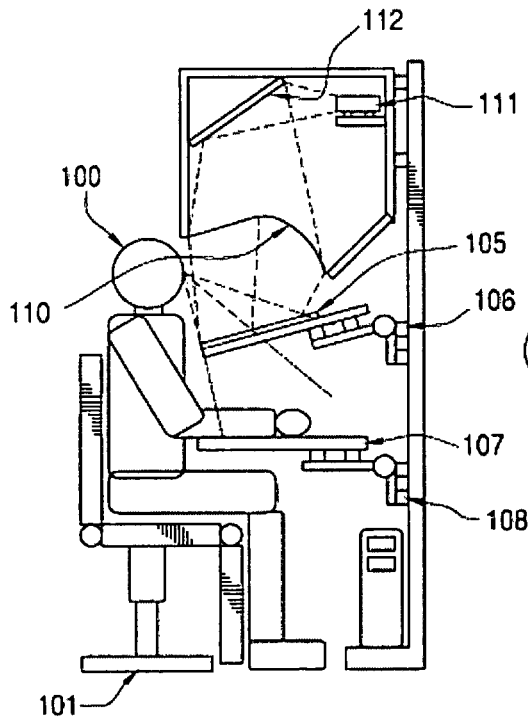
FIG. 9A shows a display unit similar to FIG. 8A, but with an alternative embodiment of the monitor so that the user can look forwards as well as downwards in the virtual environment.

FIG. 9*a* illustrates another embodiment of the display unit, which is similar to that in FIG. 7*b*. In this case, the curved screen 110 is designed for optimal viewing of the user's arms and also for viewing of objects on the virtual work surface beyond the virtual arms. This functionality is achieved by curving the rear of the curved screen 110 towards the mirror 105, so that virtual objects appear to be closer to the surface of the mirror 105 and thus higher above the virtual work surface. The difference in angle to the horizontal between the edge of the screen closest to the user and the edge of the screen furthest from the user is typically 60-90 degrees, depending on the exact desired effect. The embodiment shown here is useful in situations where the user is required to interact with other objects on the virtual work surface which lie towards the rear of the virtual work surface.

Figure 9B:
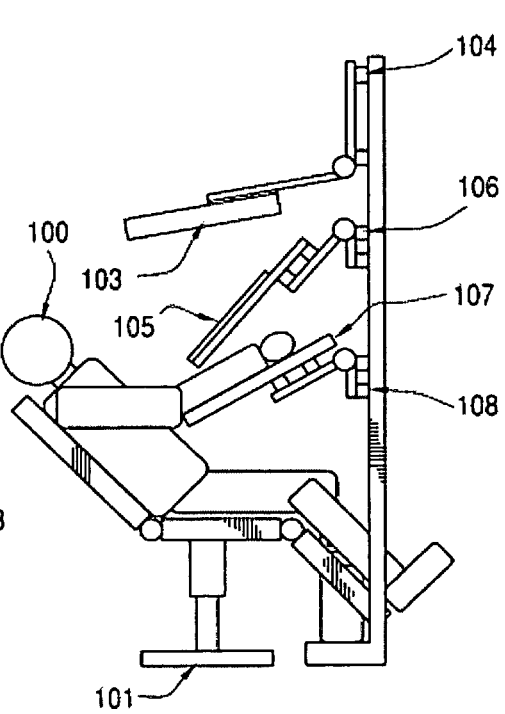
FIG. 9B shows a display unit similar to FIG. 8A, adjusted for use with the user being in a reclined position.
Figure 10:
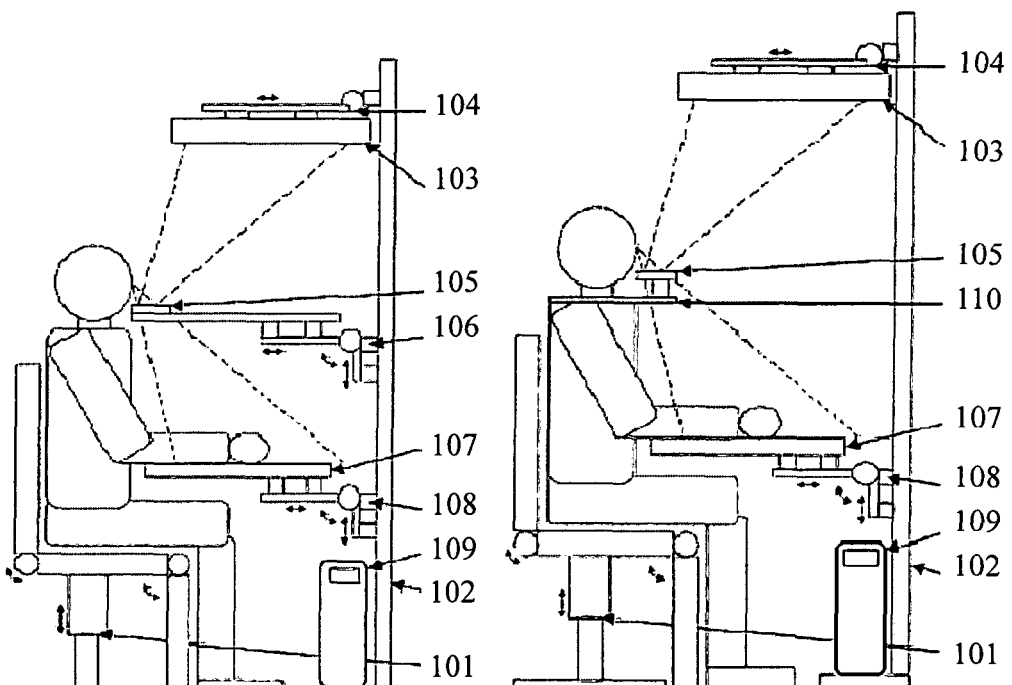
FIG. 10A shows a display unit with small mirror adjusted to be proximate to the users eyes.
FIG. 10B shows a display unit with a shoulder mounted mirror.
FIG. 10C shows a display unit in which the mirror unit comprises a prism.
Figure 10:
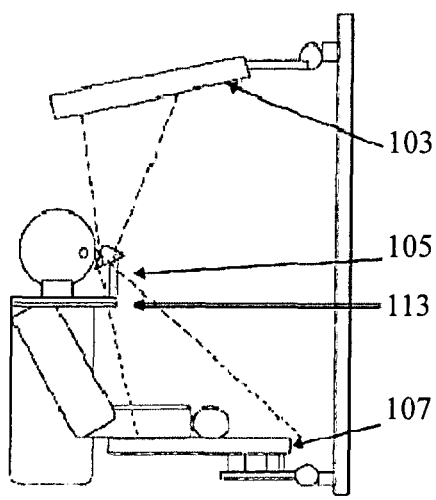

FIG. 9*b* illustrates an alternative arrangement of the display unit (as in FIG. 7*a*) for use in a reclining position. In this arrangement the chair 101 is reclined and the monitor 103, mirror 105 and work surface 107 are all inclined downwards towards the user. This arrangement can be useful in situations where it is advantageous for the user to be in a reclining position, e.g. if the user cannot sit up straight due to a medical condition, or if the user wishes to be as relaxed as possible.

It is clear that there are many other possible embodiments of the invention, and that the possible fields of application of the invention are not restricted to those mentioned above. The different features and innovations mentioned above can be combined in many different ways without departing from the spirit of the invention. It is also clear that variations in:

the mechanical properties and geometry of the materials used to construct a particular embodiment;
the specific display technology employed;
the specific arrangements of components within a particular embodiment;
the manufacturing processes used;
the details of the processing and display algorithms used; and
any other implementation detail used to construct a particular embodiment are all covered by the invention.

LEGEND: DRAWINGS

1 . . . sleeve
2 . . . attachment pad
3 . . . node
4 . . . finger base
5 . . . base cable
6 . . . node cable
7A . . . finger sensor
7B . . . finger-to-finger sensor
8 . . . finger ring
9 . . . strap
10 . . . finger guide
11 . . . finger sensor pocket
12 . . . finger base pocket
13 . . . bracket
14 . . . strut
17A . . . wrist bend sensor
17B . . . wrist rotation sensor
21 . . . vest
27A/B . . . body sensors
31 . . . shoe
31A . . . shoe sole
31B . . . shoe upper
32 . . . shoe insert
33 . . . node
34 . . . flexible band
35 . . . leg strap
36 . . . effector (feed-back element)
37A . . . foot pressure sensor
37B . . . foot bend sensor
41A . . . toe element
41B . . . heel element
41C . . . shank
42 . . . strut
43 . . . base plate
44 . . . flexible band
45 . . . leg strap
46 . . . effector
47A . . . pressure sensor
47B . . . bend sensor
47C . . . rotation sensor
48 . . . rail
49 . . . hole array
101 . . . chair
102 . . . frame
103 . . . monitor
104 . . . monitor mount
105 . . . mirror unit
106 . . . mirror mount 107 . . . work surface
108 . . . surface mount
109 . . . control computer
110 . . . curved screen
111 . . . video projector
112 . . . projector mirror
113 . . . shoulder mount

The invention claimed is:

1. An adjustable body sensor unit comprising:
   at least one node comprising at least one sensor, at least one body attachment comprising at least one attachment element for removably and adjustably attaching said at least one node to the body attachment, the body attachment being an elastic and size-adjustable body attachment glove or shoe,
   at least one element for communicating measurements received by the at least one sensor,
   wherein said element for communicating is part of the node and wherein one of a location of the node on the body attachment is adjustable and the body attachment itself is adjustable to accommodate different users,
   wherein at least one further node is adjustably attached to the body attachment and wherein the further node comprises a signal transducing element that measures a movement of a body part to which it is attached,
   wherein the at least two nodes are flexibly connected to each other,
   wherein the body attachment comprises a glove having a form of an open tube with a thumb-hole or a form of a wraparound sheet and wherein the at least one further node comprises a finger sensor or a wrist sensor; and
   wherein at least one finger-to-finger sensor is securely attached to at least two finger sensor(s), wherein said finger-to-finger sensor connects a first finger to a second finger.

2. The body sensor unit of claim 1, wherein the location of the node on the body attachment is adjustable and the body attachment itself is adjustable to accommodate different users.

3. The body sensor unit of claim 1, wherein the glove comprises one or more finger guides for receiving one or more fingers of a user.

4. The body sensor unit of claim 1, wherein the finger sensor or wrist sensor is adjustably attached via said at least one attachment element, said attachment element comprising an attachment pad, clip, zip, buttonhole or pocket.

5. The body sensor unit of claim 1, wherein said finger-to-finger sensor is securely attached at each of its two ends to a finger sensor.

6. The body sensor unit of claim 1, wherein the transducing element measures bending, rotation, elongation or pressure and is a 2D or 3D accelerometer, a magnetometer, a bend potentiometer, a linear potentiometer or a rotary potentiometer, a position encoder or a pressure sensor.

7. The body sensor unit of claim 1, wherein at least one effector is part of the at least one node.

8. The body sensor unit of claim 1, wherein the node is self powered via an energy source selected from a battery and a solar cell.

9. The body sensor unit of claim 1, wherein the node communicates with the base unit wirelessly.

10. The body sensor unit of claim 9, wherein the body sensor unit has at least one finger base, which is removably attached to the body attachment and wherein said finger base has said at least one finger sensor attached to it, wherein the finger sensor runs along a finger and is further secured to the finger(s) via sliding ring(s) at tip(s) of the finger(s).

11. The body sensor unit of claim 10, wherein said sliding ring(s) contain(s) at least one marker to track positions of said tip(s).

12. The body sensor unit of claim 11, wherein the finger sensor(s) comprise(s) an actuating device selected from a linear motor and an electroactive polymer actuator.

13. The body sensor unit of claim 1, further comprising at least one marker for detecting (a) a position, wherein the marker is selected from a magnetic field generator/detector, optical marker for an outside-in visual tracker, internal camera for inside-out visual tracker, ultrasonic emitter/receiver, and a radio transmitter/receiver, (b) an orientation, wherein the marker is selected from a magnetometer and an accelerator, and/or (c) a temperature, wherein the marker is a thermometer.

14. The body sensor unit of claim 1, wherein the body attachment is attached to a foot and measures foot movements, bending and/or forces.

15. The body sensor unit of claim 14, wherein the body attachment comprises a heel and a toe element and at least one pressure sensor and/or bend sensor at a position for contacting an external surface.

16. The body sensor unit of claim 15, wherein the body attachment is (a) an adjustable shoe or adjustable overshoe or sock, having a sole and an upper part, or (b) a toe and heel element which are adjustably attached to each other.

17. The body sensor unit of claim 15, wherein two pressure sensors are located at the toe element and two pressure sensors are located at the heel element.

18. The body sensor unit of claim 17, wherein the pressure sensors are integrated into an insert to be placed onto the sole inside the shoe and/or are placed at or into an attachment outside the shoe.

19. The body sensor unit according to claim 1, wherein the attachment element comprises a hook and loop-type connection.

20. An adjustable body sensor unit comprising:
   at least one node comprising at least one sensor, at least one body attachment comprising at least one attachment element for removably and adjustably attaching said at least one node to the body attachment, the body attachment being an elastic and size-adjustable body attachment glove or shoe,
   at least one element for communicating measurements received by the at least one sensor, wherein said element for communicating is part of the node and wherein a location of the node on the body attachment is adjustable and/or the body attachment itself is adjustable to accommodate different users,
   wherein at least one further node is adjustably attached to the body attachment and wherein the further node comprises a signal transducing element that measures a movement of a body part to which it is attached,
   wherein the at least two nodes are flexibly connected to each other, and
   wherein the attachment element comprises a hook and loop-type connection.

21. The body sensor unit of claim 20, wherein the location of the node on the body attachment is adjustable and the body attachment itself is adjustable to accommodate different users.

22. The body sensor unit of claim 20, wherein the body attachment comprises a glove having a form of an open tube with a thumb-hole or a form of a wraparound sheet and wherein the at least one further node is a finger sensor or a wrist sensor.

23. The body sensor unit of claim 22, wherein the glove comprises one or more finger guides for receiving one or more fingers of a user.

24. The body sensor unit of claim 22, wherein the finger sensor or wrist sensor is adjustably attached via said at least one attachment element, said attachment element comprising an attachment pad, clip, zip, buttonhole or pocket.

25. The body sensor unit of claim 22, wherein at least one finger-to-finger sensor is securely attached to at least two finger sensor(s), wherein said finger-to-finger sensor connects a first finger to a second finger.

26. The body sensor unit of claim 25, wherein said finger-to finger sensor is securely attached at each of its two ends to a finger sensor.

27. The body sensor unit of claim 20, wherein the transducing element measures bending, rotation, elongation or pressure and is a 2D or 3D accelerometer, a magnetometer, a bend potentiometer, a linear potentiometer or a rotary potentiometer, a position encoder or a pressure sensor.

28. The body sensor unit of claim 20, wherein at least one effector is part of the at least one node.

29. The body sensor unit of claim 20, wherein the node is self powered via an energy source selected from a battery and a solar cell.

30. The body sensor unit of claim 20, wherein the node communicates with the base unit wirelessly.

31. The body sensor unit of claim 30, wherein the body sensor unit has at least one finger base, which is removably attached to the body attachment and wherein said finger base has said at least one finger sensor attached to it, wherein the finger sensor runs along a finger and is further secured to the finger(s) via sliding ring(s) at tip(s) of the finger(s).

32. The body sensor unit of claim 31, wherein said sliding ring(s) contain(s) at least one marker to track positions of said tip(s).

33. The body sensor unit of claim 32, wherein the finger sensor(s) comprise(s) an actuating device selected from a linear motor and an electroactive polymer actuator.

34. The body sensor unit of claim 20, further comprising at least one marker for detecting (a) a position, wherein the marker is selected from a magnetic field generator/detector, optical marker for an outside-in visual tracker, internal camera for inside-out visual tracker, ultrasonic emitter/receiver, and a radio transmitter/receiver, (b) an orientation, wherein the marker is selected from a magnetometer and an accelerator, and/or (c) a temperature, wherein the marker is a thermometer.

* * * * *